United States Patent
Angerpointner et al.

(10) Patent No.: US 9,304,015 B2
(45) Date of Patent: Apr. 5, 2016

(54) SLIP-RING UNIT AND METHOD FOR MONITORING THE CONDITION OF A SLIP-RING UNIT

(71) Applicants: LTN Servotechnik GmbH, Otterfing (DE); LEINE LINDE SYSTEMS GmbH, Hamburg (DE)

(72) Inventors: Ludwig Angerpointner, Müchen (DE); Gerhard Schmid, Hamburg (DE)

(73) Assignees: LTN SERVOTECHNIK GMBH, Otterfing (DE); LEINE LINDE SYSTEMS GMBH, Hamburg (DE)

( * ) Notice: Subject to any disclaimer, the term of this patent is extended or adjusted under 35 U.S.C. 154(b) by 88 days.

(21) Appl. No.: 14/475,041

(22) Filed: Sep. 2, 2014

(65) Prior Publication Data
US 2015/0061705 A1 Mar. 5, 2015

(30) Foreign Application Priority Data
Sep. 2, 2013 (EP) .................................... 13004306

(51) Int. Cl.
*G01R 27/08* (2006.01)
*G01D 5/12* (2006.01)
*H01R 39/08* (2006.01)
*H01R 39/58* (2006.01)
*G01N 27/04* (2006.01)
*G01N 33/00* (2006.01)

(52) U.S. Cl.
CPC .................. *G01D 5/12* (2013.01); *G01N 27/04* (2013.01); *G01N 33/0004* (2013.01); *H01R 39/08* (2013.01); *H01R 39/58* (2013.01)

(58) Field of Classification Search
CPC .......... G01D 5/12; G01D 5/125; G01D 5/165; G01R 39/08; G01R 39/10; G01R 39/12; G01R 39/58; G01R 39/59
USPC .......................................... 324/511, 522, 691
See application file for complete search history.

(56) References Cited

U.S. PATENT DOCUMENTS

| 2,906,953 | A | * | 9/1959 | Stadler | ...................... G01P 3/48 324/168 |
| 5,402,461 | A | | 3/1995 | Kudo | |
| 5,633,792 | A | * | 5/1997 | Massey | ................... H02M 7/60 310/129 |

(Continued)

FOREIGN PATENT DOCUMENTS

| JP | 2012-124047 | 6/2012 |
| SU | 1328867 | 8/1987 |

(Continued)

*Primary Examiner* — Tung X Nguyen
*Assistant Examiner* — Thang Le
(74) *Attorney, Agent, or Firm* — Kenyon & Kenyon LLP

(57) ABSTRACT

A slip-ring unit for transmitting an electric current includes a first component group and a second component group arranged in a manner allowing rotation relative to each other. The slip-ring unit has a first track and a second track, a brush and a slip ring contacting each other over different rotational positions along one of the tracks. The first component group has a first connection terminal and an electric circuit for monitoring conditions, while the second component group has a second connection terminal The electric current is transmittable from the first connection terminal to the second connection terminal over the first track, and an electric voltage is transmittable over the second track to the circuit. The slip-ring unit is configured such that the first track and the second track are connected electrically.

13 Claims, 4 Drawing Sheets

(56) References Cited

U.S. PATENT DOCUMENTS

| | | | |
|---|---|---|---|
| 6,034,531 A | 3/2000 | Senglat et al. | |
| 7,285,929 B2 * | 10/2007 | Ahmed | E21B 43/128 310/68 B |
| 2014/0055153 A1 * | 2/2014 | Sato | G01R 31/34 324/750.3 |
| 2014/0197710 A1 * | 7/2014 | Ludois | H02K 19/12 310/219 |
| 2015/0175016 A2 * | 6/2015 | Tsuchiya | H02J 7/16 320/109 |

FOREIGN PATENT DOCUMENTS

| | | |
|---|---|---|
| SU | 1488902 | 6/1989 |
| WO | 2010/000350 | 1/2010 |

* cited by examiner

SLIP-RING UNIT AND METHOD FOR MONITORING THE CONDITION OF A SLIP-RING UNIT

CROSS-REFERENCE TO RELATED APPLICATIONS

The present application claims priority to Application No. 13004306.0, filed in the European Patent Office on Sep. 2, 2013, which is expressly incorporated herein in its entirety by reference thereto.

FIELD OF THE INVENTION

The present invention relates to a slip-ring unit, e.g., for transmitting an electric current between two component groups rotatable relative to each other, and to a method for monitoring the condition of such a slip-ring unit, e.g., for wind power plants.

BACKGROUND INFORMATION

Slip-ring units usually include two component groups, e.g., a stator and a rotor. The stator often includes brushes, whereas the rotor usually has a succession of slip rings. During operation, the brushes have sliding contact with rotating slip rings along what are referred to as tracks. Such slip-ring units are used in many technical fields to transmit electrical signals or electric power from a stationary unit to a rotating electrical unit.

For example, such slip-ring units are incorporated in the rotor hub or the nacelle of wind power plants to transmit control signals, for example, and/or electric currents for drives in order to adjust the angle of attack of the rotor blades.

It is especially important in the case of such high-grade plants or machines that their availability not be reduced by the slip-ring unit.

U.S. Pat. No. 6,034,531 describes a system for monitoring the wear of a rubbing electrical contact for heating the rotor blades of a helicopter.

SUMMARY

Example embodiments of the present invention provide a slip-ring unit whose condition may be monitored in a simple and economical manner.

According to example embodiments of the present invention, a slip-ring unit for transmitting an electric current includes a first component group and a second component group, the two component groups being disposed or mounted in a manner allowing rotation relative to each other about an axis. In addition, the slip-ring unit has at least one first track and at least one second track. The slip-ring unit is configured such that a brush and a slip ring contact each other over different rotational positions along one of the tracks. The first component group has a first electrical connection terminal and an electric circuit for monitoring conditions. The second component group has a second electrical connection terminal. In this context, the electric current is transmittable from the first connection terminal to the second connection terminal via the first track, e.g., the current flows over the first track. Furthermore, an electric voltage is transmittable over the second track to the circuit. The slip-ring unit is configured such that the first track and the second track are connected electrically. The circuit has a current source for generating a testing current, the slip-ring unit being configured so that the testing current flows over the first track and the second track, this electric circuit being closable by a switching element, triggered by a signal from an arithmetic logic unit.

The slip-ring unit is thus configured to transmit the electric current from the first to the second connection terminal over the first track, and to transmit the electric voltage over the second track to the circuit.

It should be understood that electric currents include electrical signals, (e.g., current having minimal amperage), currents for transmitting electric power, etc.

Releasable electrical connections such as plug-in connectors or electric couplings or clamp connections may be used as connection terminals, or perhaps also to some extent releasable or non-releasable electrical connections, for example, soldered or welded connections.

The circuit may include, for example, a switching element or a switch, especially an electronic switch or semiconductor switch, for interrupting and/or applying the testing current.

The first track may be connected electrically to the second track via a conductor or by placing the tracks on one and the same conductive slip ring. The electrical connection of the first track to the second track may have a low resistance, so that the first track and the second track have virtually the same electric potential.

A track is thus a surface along which a brush and a slip ring contact each other during the relative rotation between the first and the second component group. Accordingly, an electrical contact is produced continuously by rubbing along a track during the relative rotation. In particular, this surface or track may be disposed circumferentially on a cylindrical lateral surface of a slip ring. Alternatively, for example, in the case of what are termed disk slip rings, the track may extend circumferentially on a cylindrical end face, or a plurality of tracks may be disposed concentrically relative to the axis with different diameters.

The first component group may be arranged as a stator, while the second component group may be arranged as a rotor.

In particular, the slip-ring unit may be implemented such that the first component group has a plurality of brushes and the second component group has at least one slip ring made of electrically conductive material, especially metal. In this context, the tracks may be disposed on one and the same slip ring which is in touch contact with the plurality of brushes, e.g., two brushes.

Alternatively, the slip-ring unit may be arranged such that the second component group has at least one brush made of electrically conductive material and the first component group has a plurality of slip rings. In this context, the tracks may extend along one and the same brush which contacts two or more slip rings.

Therefore, the slip-ring unit may be implemented so that the first component group has a plurality of brushes and the second component group has at least one slip ring, or that the second component group has at least one brush and the first component group has a plurality of slip rings.

Advantageously, both the brush and the slip ring are produced from metal, especially brass, bronze, high-grade steel, a noble metal, alloys of noble metals, etc. For example, both the brush and the slip ring have a silver alloy at least in the area of the first track.

In addition, however, the tracks may also be disposed on different slip rings which are connected electrically by a conductor.

The circuit for monitoring conditions may include a device for measuring the voltage transmitted over the second track. Alternatively or additionally, the circuit may include a device for measuring the current and/or the testing current transmitted over the first track. In particular, the slip-ring unit may be configured such that during operation, the current or a signal is transmitted, and at the same time, the testing current is flowing, thereby permitting an assessment of the condition of the slip-ring unit during continuous operation, especially during predefined testing time periods.

The slip-ring unit may have a plurality of brushes and a plurality of slip rings and thus a plurality of tracks, no electric voltage being transmittable to the circuit over at least one track. Even though the slip-ring unit may have a multitude of tracks or slip rings and brushes, so that a multitude of current paths are furnished between the connection terminals, not all these current paths need to be observed by the condition monitoring. Usually, it is sufficient if one selected current path or signal path or one selected track is monitored appropriately. Advantageously, the electric current which is transmitted from the first connection terminal to the second connection terminal takes the form of an electrical signal. Therefore, the first track is to be assigned to a signal path. Thus, for example, the testing current is greater than the electric current which is transmitted from the first connection terminal to the second connection terminal.

The slip-ring unit may be configured to convey measuring signals from sensors of a rotary encoder. In particular, the rotary encoder may be integrated into the slip-ring unit. A rotary encoder may be arranged as a measuring device for measuring the relative rotational position between the first and the second component group. The rotary encoder may also be arranged such that alternatively or in addition to the instantaneous rotational position, it outputs a number of rotations between the first and the second component group that are carried out within a specific time interval. The slip-ring unit may be configured so that the measuring signals of the rotary encoder are able to be supplied to the circuit for further evaluation in the course of the condition monitoring.

In particular, the slip-ring unit may be arranged such that the slip rings are staggered relative to each other in the direction of the axis.

Example embodiments of the present invention provide a method for monitoring the condition of a slip-ring unit. In this context, the slip-ring unit includes a first and a second component group, the two component groups being disposed in a manner allowing rotation relative to each other about an axis. The slip-ring unit has a first track and a second track and is configured such that the brush and slip ring contact each other over different rotational positions along one of the tracks, so that an electric current is transmitted from a first connection terminal of the first component group to a second connection terminal of the second component group via the first track. At the same time, an electric voltage is transmitted over the second track to the circuit. The circuit monitors the condition by ascertaining a characteristic value for the condition of the slip-ring unit based on the voltage. The circuit has a current source for generating a testing current, and the slip-ring unit is configured such that the testing current flows over the first track and the second track, this electric circuit being closed by a switching element, triggered by a signal from the arithmetic logic unit.

The level of the testing current which is transmitted via the first track, or rather flows over the first track, may be determined or measured, this measured value being supplied to the circuit for the condition monitoring, so that the circuit monitors conditions by ascertaining a characteristic value for the condition of the slip-ring unit based on the voltage and the testing current transmitted over the first track.

A current source is able to generate a testing current that, for example, is conducted only intermittently over the first track and the second track, while otherwise, no such testing current flows (over the first track and the second track).

If the testing current is conducted only intermittently over the first track and the second track, the level of the testing current may be determined during this time, e.g., while the testing current is flowing over the first track and the second track.

In addition, the circuit may monitor conditions by ascertaining a characteristic value for the condition of the slip-ring unit based on the voltage which is transmitted over the second track to the circuit, and the current which is transmitted at least over the first track. In particular, a transition resistance and/or a noise level in transmitting the current may be determined and used as a characteristic value. Such characteristic values or parameters are able to provide information about the condition of the slip-ring unit.

Furthermore, a relative rotational position between the first component group and the second component group or the number of rotations between the first component group and the second component group may be measured. The resulting measuring signals may then be supplied to the circuit, so that the circuit monitors conditions by ascertaining a characteristic value for the condition of the slip-ring unit based on the voltage and the measuring signals. The number of rotations may be ascertained for a defined period of time, for example, the number may assume the value of the total number of rotations from the beginning of operation of the slip-ring unit up to the present instant. In the same manner, the rotational frequency or rotational speed during the measurement may be taken into account in forming the characteristic value, e.g., for assessing the condition of the slip-ring unit.

A relative humidity may be measured, for example, with the aid of a humidity sensor. The measured value of the relative humidity is supplied to the circuit. In addition, a temperature sensor may be disposed in the slip-ring unit, so that the dew point may be ascertained precisely, for example. In particular, in order to discover the cause of disturbances, a vibration sensor, whose signal is supplied to the circuit for the condition monitoring, may also be disposed in the slip-ring unit.

The condition is monitored by the circuit by ascertaining a characteristic value for the state of the slip-ring unit based on the voltage and the relative humidity and/or the temperature and/or the ascertained dew point and/or the vibration-sensor signals.

In particular, a limiting value may be stored in the slip-ring unit which is compared by the circuit to a characteristic value for the condition of the slip-ring unit, the slip-ring unit outputting a warning in the event the limiting value is exceeded.

The slip-ring unit may be used in a nacelle of a wind power plant, e.g., to transmit control signals and/or currents for electric drives of a rotor-blade adjustment.

Further features and aspects of example embodiments of the present invention are described in more detail below with reference to the appended Figures.

DETAILED DESCRIPTION

Figure 1:
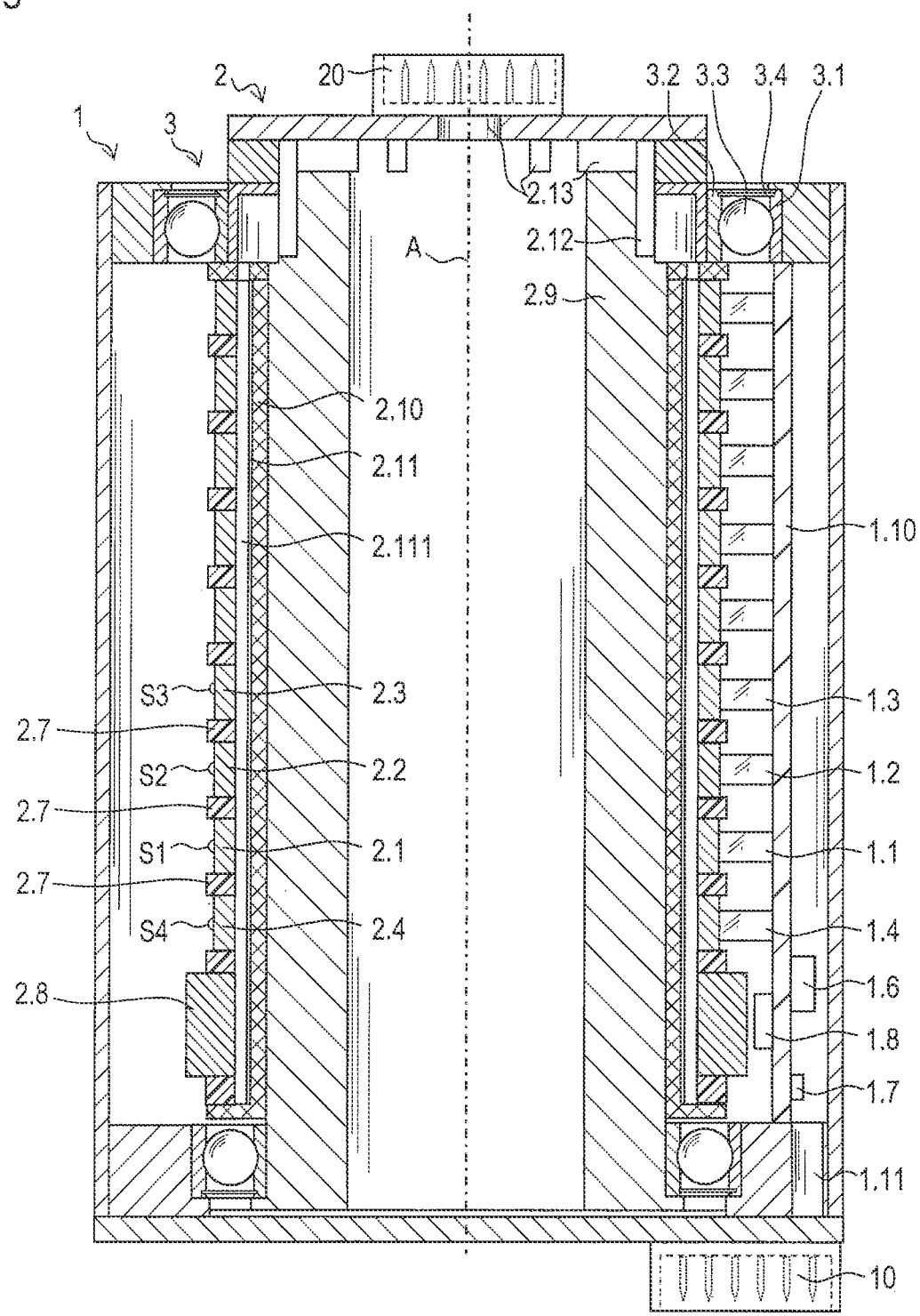
FIG. 1 is a longitudinal cross-0sectional view of a slip-ring unit.

According to FIG. 1, the slip-ring unit includes a first component group 1 which may be denoted as a stator, and a second component group 2 which acts in the following description as a rotor. The slip-ring unit is used for the multi-channel transmission of electric currents between a first electrical connection terminal 10 of first component group 1 and a second electrical connection terminal 20 of second component group 2. The two component groups 1, 2 are disposed in a manner allowing rotation relative to each other about an axis A.

Second component group 2 includes a shaft 2.9, which in the present example, takes the form of a hollow shaft. Radially outside of shaft 2.9 is, first of all, a substantially tubular component 2.10 that may be produced from aluminum, for instance. Adjacent to it further radially to the outside is a support tube 2.11 which has recesses 2.111 extending in the axial direction. Fastened to electrically insulating support tube 2.11, which preferably may be produced from plastic or ceramic, are twist-proof slip rings 2.1 to 2.4 that are disposed concentrically relative to axis A and are separated with an axial distance from each other by electrically insulating rings 2.7. For clarity, a representation of electric lines is omitted in the Figures. Notwithstanding this, in the exemplary embodiment illustrated, each of slip rings 2.1 to 2.4, mounted side-by-side with axial clearance, is connected at its inner side to an electric line, which in each case extends along a recess 2.111 in the axial direction in second component group 2, and in addition, through one of grooves 2.12 and boreholes 2.13. Accordingly, the electric lines are bonded to conductors of an electric connection terminal 20, which may be implemented as a plug-in connector and is placed at one axial end.

Besides slip rings 2.1 to 2.4, a measuring standard 2.8, which is substantially ring-shaped in the exemplary embodiment illustrated, is mounted in rotatably-fixed manner on support tube 2.11. In the exemplary embodiment illustrated, measuring standard 2.8 has a magnetic graduation or scaling on its radially outer peripheral side. The configuration is such that measuring standard 2.8 is lined up in the succession of slip rings 2.1 to 2.4, and therefore is mounted concentrically relative to axis A with axial offset with respect to slip rings 2.1 to 2.4.

First component group 1 includes electric connection terminal 10, which takes the form of a plug-in connector. Connection terminal (plug-in connector) 10 has a plurality of conductor pins, illustrated with broken lines in FIG. 1, which are connected to cables. For clarity, the cables themselves are not shown in FIG. 1. The cables are routed through a borehole 1.11 into the interior of first component group 1, and are electrically connected to conductors which are fixed in position on a holder 1.10 made of an insulating material.

Fastened to holder 1.10 are brushes 1.1 to 1.4, which are to be assigned to first component group 1 and which contact slip rings 2.1 to 2.4 in yielding fashion. Brushes 1.1 to 1.4 are produced from metal, especially a silver alloy.

Also located on holder 1.10 is an electric circuit 1.6 for monitoring conditions, as well as a scanning head 1.8 which is suitable for scanning measuring standard 2.8, e.g., with the aid of magnetoresistive sensors. In addition, a further sensor 1.7, e.g., taking the form of a humidity sensor, is provided on holder 1.10.

First component group 1 and second component group 2 are disposed in a manner allowing rotation relative to each other with the aid of rolling-contact bearings 3. Rolling-contact bearings 3 include an outer ring 3.1, an inner ring 3.2 as well as rolling elements 3.3 and, in particular, a rubbing seal 3.4.

According to the exemplary embodiment illustrated, the slip-ring unit may be mounted in a nacelle of a wind power plant and be used for transmitting electric currents S in the sense of signals, for example, in a bus system between a central control unit and a device X, e.g., a converter, on the rotor side. The signals are needed, for instance, to control electric drives or electric motors which are used to adjust the angle of attack of the rotor blades. In addition, an electric current for energy supply may be transmitted via the slip-ring unit to electric drives or electric motors that are used to adjust the angle of attack of the rotor blades. Drive motors of this type are mounted in the rotor hub of the wind power plant, and therefore rotate with the rotor of the wind power plant. First component group 1 of the slip-ring unit is thus joined in torsion-resistant fashion to the nacelle.

Since a malfunction of the slip-ring unit goes hand-in-hand with a malfunction of the entire wind power plant, it is important to monitor the condition of the slip-ring unit, so that if need be, it may be repaired or exchanged during a scheduled maintenance period.

Figure 2A:
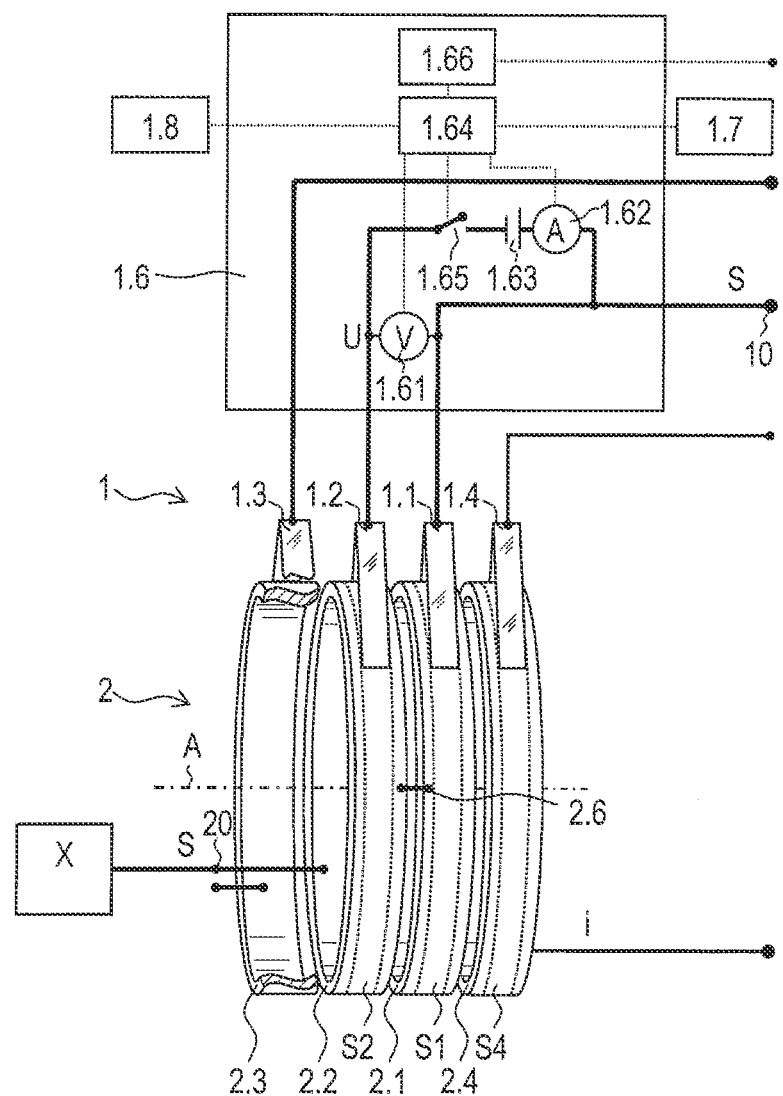
FIG. 2a schematically illustrates components of the slip-ring unit according to a first exemplary embodiment during normal operation.
Figure 2B:
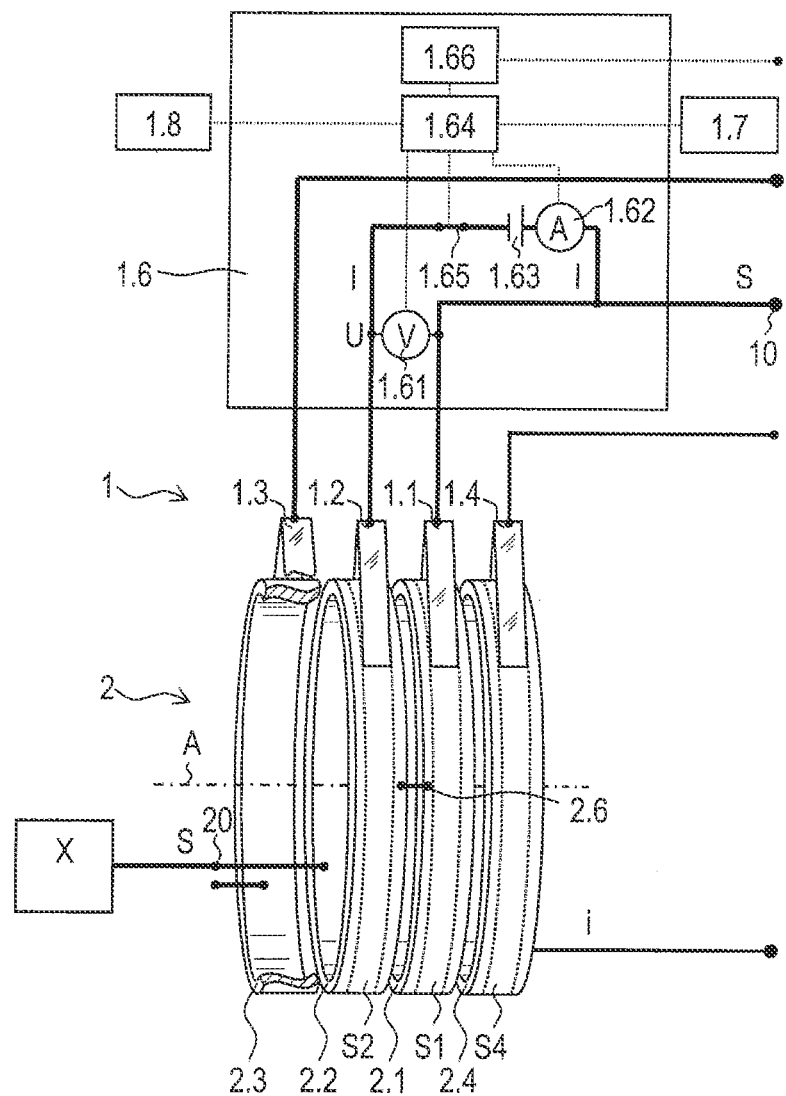
FIG. 2b schematically illustrates components of the slip-ring unit according to a first exemplary embodiment during test operation.

FIGS. 2a, 2b schematically illustrate a portion of the slip-ring unit, in which, for example, insulating rings 2.7 are not depicted for the sake of clarity. The slip-ring unit is configured such that in different rotational positions, in each case one of brushes 1.1 to 1.4 and one slip ring 2.1 to 2.4 contact each other along what are termed tracks S1, S2, S3, S4. A track should thus be understood as a cutout from the lateral surface of a slip ring 2.1 to 2.4, which in FIG. 2, is located axially between the dashed lines. In each case, one of brushes 1.1 to 1.4, in different rotational positions, e.g., during a revolution, touches associated slip ring 2.1 to 2.4 along one of these tracks S1, S2, S3, S4. In the exemplary embodiment illustrated, slip rings 2.1 to 2.4 have a silver alloy in the area of tracks S1, S2, S3, S4.

Two slip rings 2.1, 2.2 are connected electrically by a conductor 2.6, so that these slip rings 2.1 2.2 have the same electric potential, e.g., are short-circuited.

Electric current S is transmitted from first connection terminal 10 to second connection terminal 20 via first track S1 with the aid of brush 1.1 and slip ring 2.1. In addition, for example, a current i is transmitted to another power consumer via a further brush 1.4 and via another slip ring 2.4.

During operation of the wind power plant, a signal, e.g., a current S is fed by a control on the stator side, for example, via connection terminal 10 into the slip-ring unit and is transmitted by brush 1.1 along track S1 to slip ring 2.1 by rubbing. Current S flows across conductor 2.6 to adjacent slip ring 2.2. It is connected electrically to second connection terminal 20, which is disposed at second component group 2. In addition, electrical device X is connected to this second connection terminal 20.

In order to obtain information about the condition of the slip-ring unit, a testing current I is transmitted briefly at predefined time intervals (e.g., once per day) or after a certain number of rotations, via track S1 from brush 1.1 to slip ring 2.1 (see FIG. 2b). Since slip rings 2.1, 2.2 are connected electrically by conductor 2.6, testing current I flows from slip ring 2.2 to brush 1.2. For this purpose, a current source 1.63 is provided, the electric circuit in question being closed by a switching element 1.65, triggered by a signal from arithmetic logic unit 1.64. Current source 1.63 supplies direct current at comparatively low voltage, since the transition resistances are very small. For example, a battery (e.g., a rechargeable battery) together with a resistor for limiting testing current I may be used as current source 1.63.

Along track S2, an electrical connection is thus produced from slip ring 2.2 via brush 1.2 to circuit 1.6, so that a voltage U is transmittable over second track S2 from slip ring 2.2 via brush 1.2 to circuit 1.6. The applied voltage U between brushes 1.1 and 1.2 is determined by a first measuring device 1.61 and supplied to arithmetic logic unit 1.64. In addition, a second measuring device 1.62 determines the level of testing current I, this value then being supplied to an arithmetic logic unit 1.64.

Moreover, the information, obtained with the aid of scanning head 1.8, about the actual rotational speed and the number of rotations already performed by the slip-ring unit is supplied to arithmetic logic unit 1.64. The information about the relative humidity, which sensor 1.7 supplies, is passed on to arithmetic logic unit 1.64, as well.

First of all, based on the measured level of testing current I and of voltage U, a transition resistance is ascertained in arithmetic logic unit 1.64 as a characteristic value for the condition of the slip-ring unit. Especially in the first operating phrase or run-in phase of the slip-ring unit, this transition resistance may be comparatively high. However, in further operation of the slip-ring unit, the transition resistance falls back to a normal measure. By taking the rotations already performed into consideration, it can be determined, for example, that the slip-ring unit is still in the run-in phase, so that it is not necessary to output a warning. Similarly, the instantaneously measured relative humidity of the air in the slip-ring unit may be utilized to assess the transition resistance, in order to determine whether the measured transition resistance should or should not trigger a warning. Thus, by taking the rotations performed and/or the relative humidity of the air into consideration, a refined characteristic value may be ascertained for the condition of the slip-ring unit. The characteristic value is then stored in a memory 1.66, and may be read out at any time via a suitable interface by sequential electronics.

Figure 3:
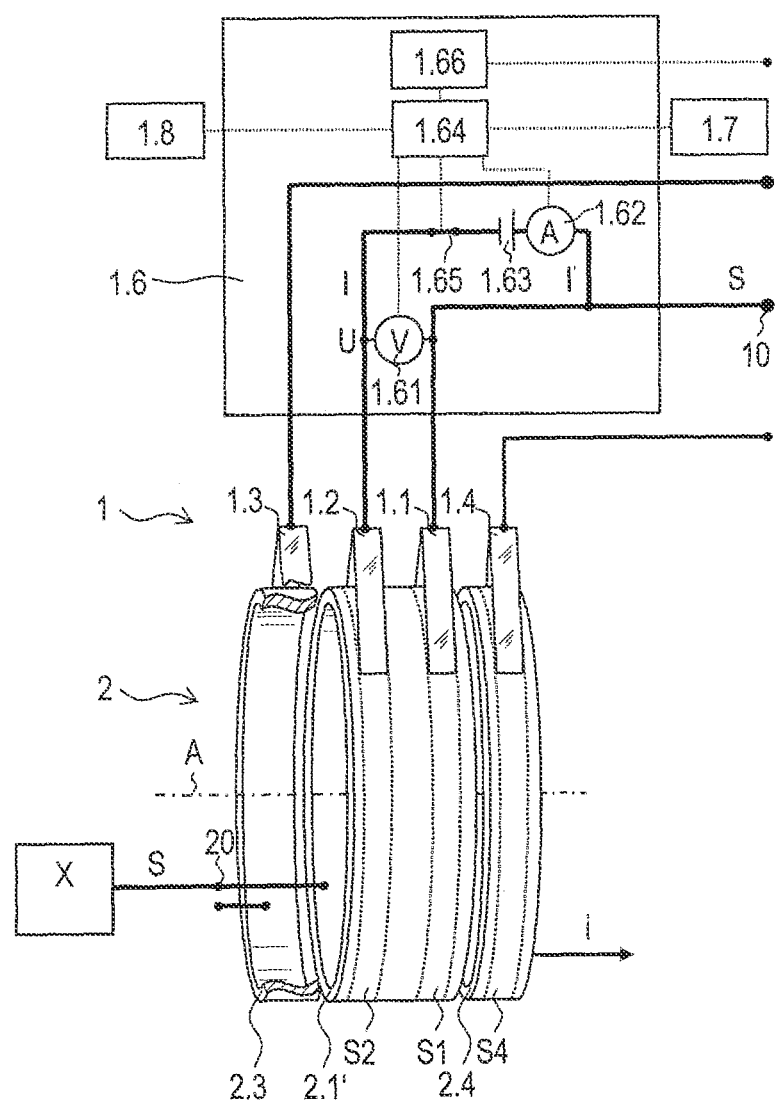
FIG. 3 schematically illustrates components of the slip-ring unit according to a second exemplary embodiment during test operation.

In a further exemplary embodiment, as illustrated in FIG. 3, the slip-ring unit includes a slip ring 2.1' which is comparatively wide in the axial direction, so that two brushes 1.1, 1.2 contact slip ring 2.1' along two tracks S1 and S2 set apart axially. Thus, two tracks S1, S2 are on slip ring 2.1'. Slip ring 2.1' is produced from electrically conductive metal and has a coating having a silver content along tracks S1, S2. Since slip ring 2.1' is electrically conductive, it is possible to dispense with a separate conductor for the electrical connection of first track S1 to second track S2. In this configuration, testing current I is transmitted by brush 1.1 along track S1 to slip ring 2.1' by rubbing. Slip ring 2.1' is connected electrically to second connection terminal 20, which is disposed at second component group 2. Electrical device X is again connected to this second connection terminal 20. Via second track S2 on slip ring 2.1', an electric voltage U is transmittable from slip ring 2.1' via brush 1.2 to circuit 1.6.

Corresponding to the first exemplary embodiment, condition monitoring may be carried out in circuit 1.6, so that based on voltage U, a characteristic value is ascertained for the condition of the slip-ring unit, possibly in consideration of the rotations executed or the relative humidity of the air in the slip-ring unit.

What is claimed is:

1. A slip-ring unit for transmitting an electric current, comprising:
    a first component group;
    a second component group, the two component groups arranged in a manner allowing rotation relative to each other about an axis;
    a first track;
    a second track;
    a brush; and
    a slip ring, the brush and the slip ring arranged to contact each other over different rotational positions along one of the tracks;
    wherein the first component group includes a first connection terminal and an electric circuit adapted to monitor conditions;
    wherein the second component group includes a second connection terminal;
    wherein the electric current is transmittable from the first connection terminal to the second connection terminal over the first track;
    wherein an electric voltage is transmittable over the second track to the circuit;
    wherein the first track and the second track are connected electrically; and
    wherein the circuit includes a current source adapted to generate a testing current, and the slip-ring unit is configured such that the testing current flows over the first track and the second track, the circuit being closable by a switching device, triggered by a signal from an arithmetic logic unit.

2. The slip-ring unit according to claim 1, wherein the tracks are arranged on a common slip ring.

3. The slip-ring unit according to claim 1, wherein the tracks are arranged on different slip rings, connected electrically by a conductor.

4. The slip-ring unit according to claim 1, wherein the circuit includes a voltage-measurement device.

5. The slip-ring unit according to claim 1, wherein the circuit includes a measurement device adapted to measure the testing current.

6. The slip-ring unit according to claim 1, wherein the slip-ring unit is configured such that measuring signals from sensors of a rotary encoder are suppliable to the circuit.

7. The slip-ring unit according to claim 1, wherein the slip-ring unit includes a rotary encoder adapted to measure a relative rotational position between the first component group and the second component group and/or a number of rotations between the first component group and the second component group, measuring signals of the rotary encoder being suppliable to the circuit.

8. A method for monitoring a condition of a slip-ring unit, the slip-ring unit including a first component group and a second component group, the two component groups being arranged in a manner allowing rotation relative to each other about an axis, the slip-ring unit having a first track and a second track, and having a brush and a slip ring that contact each other over different rotational positions along one of the tracks, comprising:
    transmitting an electric current over the first track from a first connection terminal of the first component group to a second current connection terminal of the second component group;
    transmitting an electric voltage over the second track to the circuit; and
    monitoring conditions, by the circuit, by ascertaining a characteristic value for the condition of the slip-ring unit based on the voltage, the circuit having a current source adapted to generate a testing current, and the slip-ring unit being configured such that the testing current flows over the first track and the second track, the circuit being closable by a switching device, triggered by a signal from an arithmetic logic unit.

9. The method according to claim 8, further comprising conducting the testing current, generated by the current source, over the first track and the second track.

10. The method according to claim 9, wherein the testing current is conducted only intermittently over the first track and the second track.

11. The method according to claim 8, further comprising:
measuring a relative rotational position between the first component group and the second component group and/or a number of rotations between the first component group and the second component group;
supplying resulting measuring signals to the circuit; and
monitoring the condition, by the circuit, by ascertaining a characteristic value for the condition of the slip-ring unit based on the voltage and the measuring signals.

12. The method according to claim 8, further comprising:
measuring a relative humidity;
supplying a measured value of the relative humidity to the circuit; and
monitoring the condition, by the circuit, by ascertaining a characteristic value for the condition of the slip-ring unit based on the voltage and the relative humidity.

13. The method according to claim 8, further comprising:
comparing, by the circuit, a limiting value stored in the slip-ring unit to a characteristic value for the condition of the slip-ring unit; and
outputting a warning being output by the slip-ring unit in response to the limiting value being exceeded.

* * * * *